US011412781B2

(12) United States Patent
Davis et al.

(10) Patent No.: US 11,412,781 B2
(45) Date of Patent: Aug. 16, 2022

(54) ADAPTERS FOR REFILLING AN AEROSOL DELIVERY DEVICE

(71) Applicant: RAI STRATEGIC HOLDINGS, INC., Winston-Salem, NC (US)

(72) Inventors: Michael F. Davis, Clemmons, NC (US); Percy D. Phillips, Pfafftown, NC (US); James William Rogers, Winston-Salem, NC (US); Lisa E. Brown, Lexington, NC (US); James Demopolous, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 461 days.

(21) Appl. No.: 15/042,868

(22) Filed: Feb. 12, 2016

(65) Prior Publication Data

US 2017/0231274 A1    Aug. 17, 2017

(51) Int. Cl.
  *B65B 3/14*    (2006.01)
  *B65B 39/00*   (2006.01)
  (Continued)

(52) U.S. Cl.
  CPC ............... *A24F 40/00* (2020.01); *B65B 3/14* (2013.01); *B65B 39/004* (2013.01); (Continued)

(58) Field of Classification Search
  CPC ....... A24F 47/008; B65B 39/004; B65B 3/12; B65B 3/10; B65B 3/04
  (Continued)

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report dated Apr. 18, 2017 for International Application No. PCT/IB2017/050722.

*Primary Examiner* — Kelly M Gambetta
*Assistant Examiner* — Russell E Sparks
(74) *Attorney, Agent, or Firm* — Womble Bond Dickinson (US) LLP

(57) ABSTRACT

Adapters for refilling an aerosol delivery device are provided. The adapters comprise a body having a container-side end and an opposing, device-side end that are sealably connectable with respectively a container of aerosol precursor composition and an aerosol delivery device having a refillable reservoir. The body defines a passageway between the ends for transfer of aerosol precursor composition from the container into the refillable reservoir. In one adapter, the container-side end is configured to engage a valve of the container during refilling of the reservoir, and thereby defines separate and distinct filling and mating ports. In another adapter, the device-side end includes a valve configured to engage the aerosol delivery device during refilling of the reservoir in which the airflow port of the aerosol delivery device is closed by the valve to prevent the aerosol precursor composition from passing through the airflow port.

18 Claims, 10 Drawing Sheets

Figure 1A:
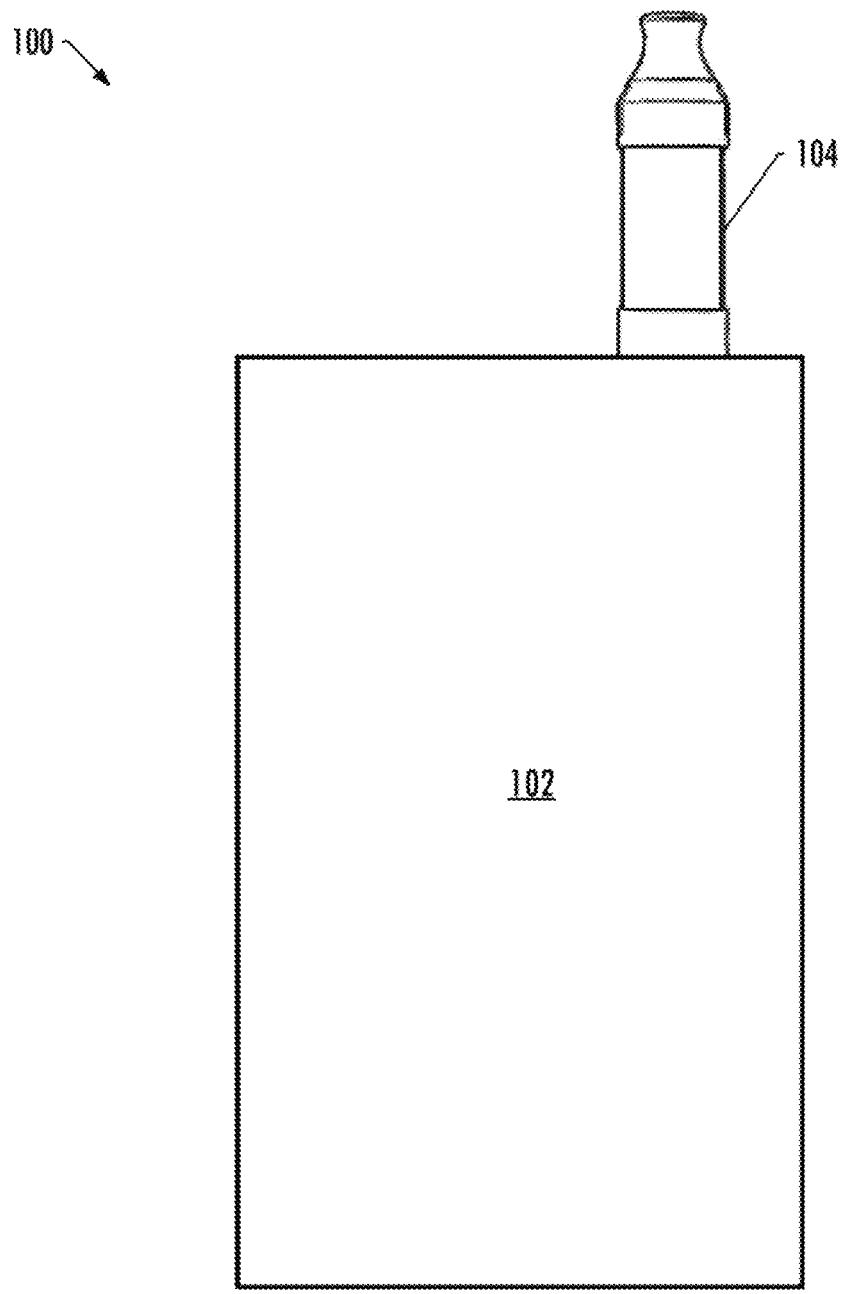

(51) Int. Cl.
*A24F 15/015* (2020.01)
*A24F 40/00* (2020.01)
*A24F 40/10* (2020.01)

(52) U.S. Cl.
CPC ............ *A24F 15/015* (2020.01); *A24F 40/10* (2020.01); *A61M 2209/045* (2013.01)

(58) Field of Classification Search
USPC ........................................................ 131/329
See application file for complete search history.

(56) References Cited

U.S. PATENT DOCUMENTS

| | | | |
|---|---|---|---|
| 2,104,266 A | 1/1938 | McCormick | |
| 3,045,671 A * | 7/1962 | Updegraff | A62B 7/00 128/205.21 |
| 3,200,819 A | 8/1965 | Gilbert | |
| 3,721,240 A * | 3/1973 | Tamburri | A61M 15/06 128/202.21 |
| 4,284,089 A | 8/1981 | Ray | |
| 4,303,083 A | 12/1981 | Burruss, Jr. | |
| 4,393,884 A * | 7/1983 | Jacobs | A24F 47/002 128/200.23 |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,381,836 A * | 1/1995 | Braatz | A61M 16/183 141/21 |
| 5,388,574 A | 2/1995 | Ingebrethsen et al. | |
| 5,408,574 A | 4/1995 | Deevi et al. | |
| 5,468,936 A | 11/1995 | Deevi et al. | |
| 5,498,850 A | 3/1996 | Das | |
| 5,515,842 A | 5/1996 | Ramseyer et al. | |
| 5,530,225 A | 6/1996 | Hajaligol | |
| 5,564,442 A | 10/1996 | MacDonald et al. | |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiring et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,196,219 B1 | 3/2001 | Hess et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,854,461 B2 | 2/2005 | Nichols | |
| 6,854,470 B1 | 2/2005 | Pu | |
| 7,117,867 B2 | 10/2006 | Cox et al. | |
| 7,293,565 B2 | 11/2007 | Griffin et al. | |
| 7,513,253 B2 | 4/2009 | Kobayashi et al. | |
| 7,775,459 B2 | 8/2010 | Martens, III et al. | |
| 7,832,410 B2 | 11/2010 | Hon | |
| 7,845,359 B2 | 12/2010 | Montaser | |
| 7,896,006 B2 | 3/2011 | Hamano et al. | |
| 8,127,772 B2 | 3/2012 | Montaser | |
| 8,314,591 B2 | 11/2012 | Terry et al. | |
| 8,365,742 B2 | 2/2013 | Hon | |
| 8,402,976 B2 | 3/2013 | Fernando et al. | |
| 8,499,766 B1 | 8/2013 | Newton | |
| 8,505,548 B2 | 8/2013 | Hearn | |
| 8,528,569 B1 | 9/2013 | Newton | |
| 8,550,069 B2 | 10/2013 | Alelov | |
| 8,757,169 B2 | 6/2014 | Gysland | |
| 8,910,639 B2 | 12/2014 | Chang et al. | |
| 9,022,039 B2 | 5/2015 | Hearn | |
| D769,519 S * | 10/2016 | Chen | D27/101 |
| 9,668,522 B2 * | 6/2017 | Memari | A24F 15/12 |
| 2002/0146242 A1 | 10/2002 | Vieira | |
| 2003/0096083 A1 * | 5/2003 | Morgan | B05D 5/08 428/141 |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0200488 A1 | 10/2004 | Felter et al. | |
| 2004/0226568 A1 | 11/2004 | Takeuchi et al. | |
| 2005/0016550 A1 | 1/2005 | Katase | |
| 2005/0170098 A1 * | 8/2005 | Baumann | B08B 17/06 427/372.2 |
| 2006/0016453 A1 | 1/2006 | Kim | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2007/0267031 A1 | 11/2007 | Hon | |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0255534 A1 | 10/2009 | Paterno | |
| 2009/0272379 A1 | 11/2009 | Thorens et al. | |
| 2009/0283103 A1 | 11/2009 | Nielsen et al. | |
| 2009/0320863 A1 | 12/2009 | Fernando et al. | |
| 2010/0043809 A1 | 2/2010 | Magnon | |
| 2010/0083959 A1 | 4/2010 | Siller | |
| 2010/0200006 A1 | 8/2010 | Robinson et al. | |
| 2010/0229881 A1 * | 9/2010 | Hearn | A24F 47/002 131/273 |
| 2010/0242974 A1 | 9/2010 | Pan | |
| 2010/0242975 A1 * | 9/2010 | Hearn | A24F 47/002 131/273 |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0011396 A1 | 1/2011 | Fang | |
| 2011/0036363 A1 | 2/2011 | Urtsev et al. | |
| 2011/0036365 A1 | 2/2011 | Chong et al. | |
| 2011/0087164 A1 * | 4/2011 | Mosler | A61J 1/2089 604/87 |
| 2011/0094523 A1 | 4/2011 | Thorens et al. | |
| 2011/0126848 A1 | 6/2011 | Zuber et al. | |
| 2011/0155153 A1 | 6/2011 | Thorens et al. | |

(56) References Cited

U.S. PATENT DOCUMENTS

| | | |
|---|---|---|
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2011/0315152 A1* | 12/2011 | Hearn ............... A24F 47/002 131/273 |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0167906 A1* | 7/2012 | Gysland ............ A24F 47/008 131/328 |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0285476 A1 | 11/2012 | Hon |
| 2012/0318882 A1 | 12/2012 | Abehasera |
| 2013/0037041 A1 | 2/2013 | Worm et al. |
| 2013/0037042 A1 | 2/2013 | Hearn et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0087160 A1* | 4/2013 | Gherghe ............... A24F 1/00 131/329 |
| 2013/0192618 A1 | 8/2013 | Li et al. |
| 2013/0192619 A1 | 8/2013 | Tucker et al. |
| 2013/0213420 A1 | 8/2013 | Hon |
| 2013/0255702 A1 | 10/2013 | Griffith, Jr. et al. |
| 2013/0269684 A1* | 10/2013 | Patton ............. A61M 15/0085 128/200.16 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0076310 A1* | 3/2014 | Newton ............. A61M 15/06 128/202.21 |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0123989 A1* | 5/2014 | LaMothe ........... A24F 47/008 131/328 |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0283859 A1* | 9/2014 | Minskoff ........... A24F 47/008 131/329 |
| 2014/0283946 A1* | 9/2014 | Kribs ................. B65D 47/06 141/2 |
| 2014/0345631 A1 | 11/2014 | Bowen et al. |
| 2015/0053217 A1 | 2/2015 | Steingraber et al. |
| 2015/0097513 A1 | 4/2015 | Liberti et al. |
| 2015/0117841 A1* | 4/2015 | Brammer ............ H05B 3/02 392/387 |
| 2015/0128974 A1 | 5/2015 | Hon |
| 2015/0144145 A1 | 5/2015 | Chang et al. |
| 2015/0231108 A1 | 8/2015 | Hearn et al. |
| 2015/0257446 A1* | 9/2015 | Chung ............... A24F 47/008 131/329 |
| 2015/0282530 A1* | 10/2015 | Johnson ............. A61M 15/06 392/387 |
| 2015/0342258 A1* | 12/2015 | Chen ................... H05B 3/06 131/329 |
| 2016/0068379 A1* | 3/2016 | Desoutter ........... B29C 49/58 141/1 |
| 2016/0095355 A1* | 4/2016 | Hearn ................. A24F 47/008 131/273 |
| 2016/0120227 A1* | 5/2016 | Levitz ................ A24F 47/008 219/386 |
| 2016/0128384 A1* | 5/2016 | Luciani .............. A24F 47/008 131/329 |
| 2016/0270446 A1* | 9/2016 | Shenkal ............. A24F 47/008 |
| 2016/0332754 A1* | 11/2016 | Brown ................. B65B 3/10 |
| 2017/0001854 A1* | 1/2017 | Li ..................... B65D 47/265 |
| 2017/0013880 A1* | 1/2017 | O'Brien ............. A24F 47/008 |
| 2017/0086502 A1* | 3/2017 | Hearn ................. A24F 47/008 |
| 2017/0136660 A1* | 5/2017 | Heilmann .......... B29C 33/3842 |
| 2017/0231274 A1* | 8/2017 | Davis ................. A24F 47/008 141/2 |
| 2017/0273360 A1* | 9/2017 | Brinkley ............... A24F 7/00 |
| 2017/0290368 A1* | 10/2017 | Hearn ................. A24F 47/002 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 103025375 A | 4/2013 |
| CN | 103330288 A | 10/2013 |
| CN | 204409585 U | 6/2015 |
| CN | 105073062 A | 11/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| JP | 2015-523077 A | 8/2015 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | 2009001082 A1 | 12/2008 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2014/155089 | 10/2014 |
| WO | WO 2014/155090 | 10/2014 |
| WO | WO 2014/155092 | 10/2014 |
| WO | WO 2014/155095 | 10/2014 |
| WO | 2015/117062 A1 | 8/2015 |
| WO | 2015/128665 A1 | 9/2015 |
| WO | WO 2015/157224 | 10/2015 |
| WO | WO-2016128562 A1 * | 8/2016 ............ A61M 15/06 |
| WO | WO-2016128717 A1 * | 8/2016 ............ A61M 15/06 |

\* cited by examiner

```
                              START
                                │
                                ▼
┌─────────────────────────────────────────────────────────────┐
│ SEALABLY CONNECTING AN ADAPTER WITH THE CONTAINER AND AEROSOL│
│ DELIVERY DEVICE, THE ADAPTER COMPRISING A BODY HAVING A MATING END│
│ AND AN OPPOSING INTERFACE END THAT ARE SEALABLY CONNECTABLE WITH │
│ RESPECTIVELY THE CONTAINER AND AEROSOL DELIVERY DEVICE, AND THE BODY│
│ DEFINING A PASSAGEWAY THEREBETWEEN FOR TRANSFER OF AEROSOL  │
│ PRECURSOR COMPOSITION FROM THE CONTAINER INTO THE REFILLABLE│
│                          RESERVOIR                          │
│                             802                             │
└─────────────────────────────────────────────────────────────┘
                                │
                                ▼
┌─────────────────────────────────────────────────────────────┐
│ TRANSFERRING AEROSOL PRECURSOR COMPOSITION FROM THE CONTAINER│
│ THROUGH THE PASSAGEWAY AND INTO THE RESERVOIR TO THEREBY REFILL THE│
│                          RESERVOIR                          │
│                             804                             │
└─────────────────────────────────────────────────────────────┘
                                │
                                ▼
                               END
```

FIG. 8

ADAPTERS FOR REFILLING AN AEROSOL DELIVERY DEVICE

TECHNOLOGICAL FIELD

The present disclosure relates to aerosol delivery devices such as smoking articles that may utilize electrically generated heat for the production of aerosol (e.g., smoking articles commonly referred to as electronic cigarettes). The smoking articles may be configured to heat the aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2013/0056013 to Terry et al., 2013/0192618 to Li et al., 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference. Moreover, various types of systems and methods for refilling electrically powered aerosol and vapor delivery devices have been proposed in U.S. Pat. No. 8,757,169 to Gysland and U.S. Pat. No. 9,022,039 to Hearn; U.S. Pat. Pub. Nos. 2007/0267031 to Hon, 2011/0315152 to Hearn et al., and 2014/0076310 to Newton; and PCT Pub. Nos. 2015/157224 to Johnson et al. and 2014/155095 to Hearn et al.; all of which are incorporated herein by reference.

It would be desirable to provide adapters to mate non-compatible components (e.g., a non-compatible aerosol delivery device and container of aerosol precursor composition) for refilling an aerosol delivery device.

SUMMARY OF THE DISCLOSURE

The present disclosure relates to aerosol delivery devices, methods of forming such devices, and elements of such devices. The present disclosure thus includes, without limitation, the following example implementations. In some example implementations, an adapter is provided for mating a container of aerosol precursor composition with an aerosol delivery device having a refillable reservoir. The adapter includes a body having a container-side end and an opposing device-side end that are sealably connectable with respectively the container and aerosol delivery device. The body defines a passageway between the container-side and device-side ends for transfer of aerosol precursor composition from the container into the refillable reservoir. The container-side end is configured to engage a valve of the container during refilling of the reservoir. The container-side end defines separate and distinct filling and mating ports. The filling port being for transfer of aerosol precursor composition from the container into the refillable reservoir during engagement of the container-side end and valve, and the mating port defining an inner cavity sized to receive therein a matching portion of the valve for connection therewith.

In some example implementations of the adapter of the preceding or any subsequent example implementation, or any combination thereof, the container-side end includes an adapter protrusion defining the mating port therein, and the container includes a nozzle within which the valve is movably positioned. The nozzle includes a cavity sized to receive therein at least a portion of the valve when the container-side end and valve are disengaged, and the adapter protrusion when the container-side end and valve are engaged.

In some example implementations of the adapter of any preceding or any subsequent example implementation, or any combination thereof, the nozzle includes a spout containing a micro-patterned internal surface therein for transfer of aerosol precursor composition from the container into the reservoir, and the filling port is sized to receive the spout when the container-side end and valve are engaged.

In some example implementations of the adapter of any preceding or any subsequent example implementation, or any combination thereof, the container-side end further includes a slot mateable with a matching tab of the container to align the container-side end with the container for connection therewith.

In some example implementations of the adapter of any preceding or any subsequent example implementation, or any combination thereof, the device-side end defines an intermediary reservoir between the passageway and the aerosol delivery device upon engaging the aerosol delivery device. The intermediary reservoir defines a compressible body configured to receive aerosol precursor composition from the container via the passageway, and in response to being compressed, force at least some of the aerosol precursor composition from the intermediary reservoir into the refillable reservoir.

In some example implementations of the adapter of any preceding or any subsequent example implementation, or any combination thereof, the device-side end is internally threaded, and the device-side end is sealably connectable with the aerosol delivery device includes being threadable onto an externally threaded portion of the aerosol delivery device. The externally threaded portion defines an opening to the refillable reservoir of the aerosol delivery device.

In some example implementations of the adapter of any preceding or any subsequent example implementation, or any combination thereof, at least an inner cavity of the device-side end defines a sheath sized to receive at least a portion of the aerosol delivery device therein.

In some example implementations, an adapter is provided for mating a container of aerosol precursor composition with an aerosol delivery device having a refillable reservoir. The adapter includes a body having a container-side end and an opposing device-side end that are sealably connectable with respectively the container and aerosol delivery device. The body defines a passageway between the container-side and device-side ends for transfer of aerosol precursor composition from the container into the refillable reservoir. The device-side end includes a valve configured to engage the aerosol delivery device during refilling of the reservoir. The aerosol delivery device defines separate and distinct filling and airflow ports. The filling port being for transfer aerosol precursor composition from the container into the refillable reservoir during engagement of the valve and the aerosol delivery device in which the airflow port is closed by the valve to prevent the aerosol precursor composition from passing through the airflow port, and the airflow port being for a flow of air through a portion of the aerosol delivery device when the valve and aerosol delivery device are disengaged.

In some example implementations of the adapter of the preceding or any subsequent example implementation, or any combination thereof, the valve includes a depressible valve body including a first valve member and a second valve member. The first valve member is for opening a passageway to aerosol precursor composition within the container, and the second valve member is for closing the airflow port, when the valve body is depressed. The airflow port defines an inner cavity, and the second valve member includes a matching portion. The inner cavity is sized to receive therein the matching portion of the second valve member.

In some example implementations of the adapter of any preceding or any subsequent example implementation, or any combination thereof, the aerosol delivery device includes an adapter protrusion defining the airflow port, and the device-side end includes a nozzle within which the valve is movably positioned. The nozzle includes a cavity sized to receive therein at least a portion of the valve when the valve and aerosol delivery device are disengaged, and the adapter protrusion when the valve and aerosol delivery device are engaged.

In some example implementations of the adapter of any preceding or any subsequent example implementation, or any combination thereof, the nozzle includes a spout containing a micro-patterned internal surface for transfer of aerosol precursor composition from the container into the aerosol delivery device, and the filling port is sized to receive the spout when the valve and aerosol delivery device are engaged.

In some example implementations of the adapter of any preceding or any subsequent example implementation, or any combination thereof, the device-side end further includes a tab mateable with a matching slot of the aerosol delivery device to align the device-side end with the aerosol delivery device for connection therewith.

In some example implementations of the adapter of any preceding or any subsequent example implementation, or any combination thereof, the device-side end defines one or more liquid ports configured to allow the transfer of aerosol precursor composition from the passageway into the device-side end.

In some example implementations of the adapter of any preceding or any subsequent example implementation, or any combination thereof, the container-side end defines an intermediary reservoir between the passageway and the container upon connection with the container. The intermediary reservoir defines a compressible body configured to receive aerosol precursor composition from the container, and in response to being compressed, force at least some of the aerosol precursor composition from the intermediary reservoir into the device-side end via the passageway.

In some example implementations of the adapter of any preceding or any subsequent example implementation, or any combination thereof, the container-side end is internally threaded, and the container-side end is sealably connectable with the container includes being threadable onto an externally threaded portion of the container. The externally threaded portion defines an opening to a reservoir of aerosol precursor composition of the container.

In some example implementations of the adapter of any preceding or any subsequent example implementation, or any combination thereof, at least an inner cavity of the container-side end defines a sheath sized to receive the container therein.

In some example implementations, a method of mating a container of aerosol precursor composition with an aerosol delivery device having a refillable reservoir for refilling the aerosol delivery device is provided. The method includes sealably connecting an adapter with the container and aerosol delivery device, the adapter comprising a body having a container-side end and an opposing device-side end that are sealably connectable with respectively the container and aerosol delivery device, and the body defining a passageway between the container-side end and device-side ends for transfer of aerosol precursor composition from the container into the refillable reservoir. The method also includes transferring aerosol precursor composition from the container through the passageway and into the reservoir to thereby refill the reservoir in which the container-side end is configured to engage a valve of the container during refilling of the reservoir. The container-side end defines separate and distinct mating and filling ports, the mating port defining an inner cavity sized to receive therein a matching portion of the valve for connection therewith, the filling port being for transfer of aerosol precursor composition from the container into the refillable reservoir during engagement of the container-side end and valve.

In some example implementations of the method of the preceding or any subsequent example implementation, or any combination thereof, the container-side end includes an adapter protrusion defining the mating port therein, and the container includes a nozzle within which the valve is movably positioned, the nozzle including a cavity sized to receive therein at least a portion of the valve when the container-side end and valve are disengaged, and the adapter protrusion when the container-side end and valve are engaged.

In some example implementations, a method for refilling an aerosol delivery device of mating a container of aerosol precursor composition with an aerosol delivery device having a refillable reservoir for refilling the aerosol delivery device is provided. The method includes sealably connecting an adapter with the container and aerosol delivery device. The adapter comprises a body having a container-side end and an opposing device-side end that are sealably connectable with respectively the container and aerosol delivery device, and the body defines a passageway between the container-side and device-side ends for transfer of aerosol precursor composition from the container into the refillable reservoir. The method also includes transferring aerosol precursor composition from the container through the passageway and into the reservoir to thereby refill the reservoir in which the device-side end includes a valve configured to engage the aerosol delivery device during refilling of the reservoir. The aerosol delivery device defines separate and distinct airflow and filling ports. The airflow port is for a flow of air through a portion of the aerosol delivery device when the valve and aerosol delivery device are disengaged. The filling port being for transfer aerosol precursor composition from the container into the refillable reservoir during engagement of the valve and the aerosol delivery device in which the airflow port is closed by the valve to prevent the aerosol precursor composition from passing through the airflow port.

In some example implementations of the method of the preceding or any subsequent example implementation, or any combination thereof, the valve includes a depressible valve body including a first valve member and a second valve member. The first valve member is for opening a passageway to aerosol precursor composition within the container, and the second valve member being for closing the airflow port, when the valve body is depressed. The airflow port defines an inner cavity, and the second valve member includes a matching portion in which the inner cavity is sized to receive therein the matching portion of the second valve member.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Having thus described the disclosure in the foregoing general terms, reference will now be made to the accompanying drawings, which are not necessarily drawn to scale, and wherein:

FIG. 1A illustrates a front view of aerosol delivery device including a tank coupled to a control body according to an example implementation of the present disclosure;

FIG. 1B illustrates a sectional view of the aerosol delivery device of FIG. 1;

FIG. 2 illustrates a perspective view of an aerosol delivery device, according to an example implementation of the present disclosure;

FIG. 3 illustrates a container of aerosol precursor composition including a reservoir according to an example implementation of the present disclosure;

FIG. 4 illustrates an adapter for mating a container of aerosol precursor composition with an otherwise incompatible aerosol delivery device according to an example implementation of the present disclosure;

FIG. 5 illustrates an adapter for mating an aerosol delivery device with an otherwise incompatible container of aerosol precursor composition according to an example implementation of the present disclosure;

FIG. 6 illustrates an apparatus defining structural elements of at least a portion of a suitable aerosol delivery device or the adapter of FIG. 4, according to an example implementation of the present disclosure;

FIGS. 7A-7D illustrate an apparatus defining structural elements of at least a portion of a suitable container or the adapter of FIG. 5; and FIG. 8 illustrates various operations in a method for implementing a contained liquid system for use with a refillable aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Aerosol delivery devices are often configured in a manner that mimics aspects of certain traditional smoking devices such as cigarettes or cigars. In this regard, aerosol delivery devices typically define a substantially cylindrical configuration. Typically, an elongated body resembling the shape of a cigarette or cigar can be formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. Aerosol delivery devices often include a control body and a cartridge which attach in an end-to-end relationship to define the substantially cylindrical configuration.

While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, the cylindrical configuration may result in the mouthpiece being exposed to the surrounding environment and therefore susceptible to contamination. Accordingly, it may be desirable to provide aerosol delivery devices in configurations that differ from shapes associated with traditional smoking articles.

In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

In various examples, an aerosol delivery device can comprise a reservoir configured to retain the aerosol precursor composition. The reservoir particularly can be formed of a porous material (e.g., a rigid porous material or primarily fibrous material) and thus may be referred to as a porous substrate.

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. In further example implementations, organic cotton, polyethylene terephthalate, regenerated cellulose, porous ceramic or glass, or porous sintered ceramic or glass can be used. A reservoir may be substantially in the form of a container and may include a fibrous material included therein.

In some implementations, the aerosol delivery device can include an indicator, which may comprise one or more light emitting diodes or a graphical user interface via a display. The indicator can be in communication with the control component through a connector circuit and illuminate, for example, during a user draw on the mouthend as detected by the flow sensor.

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

Figure 1B:
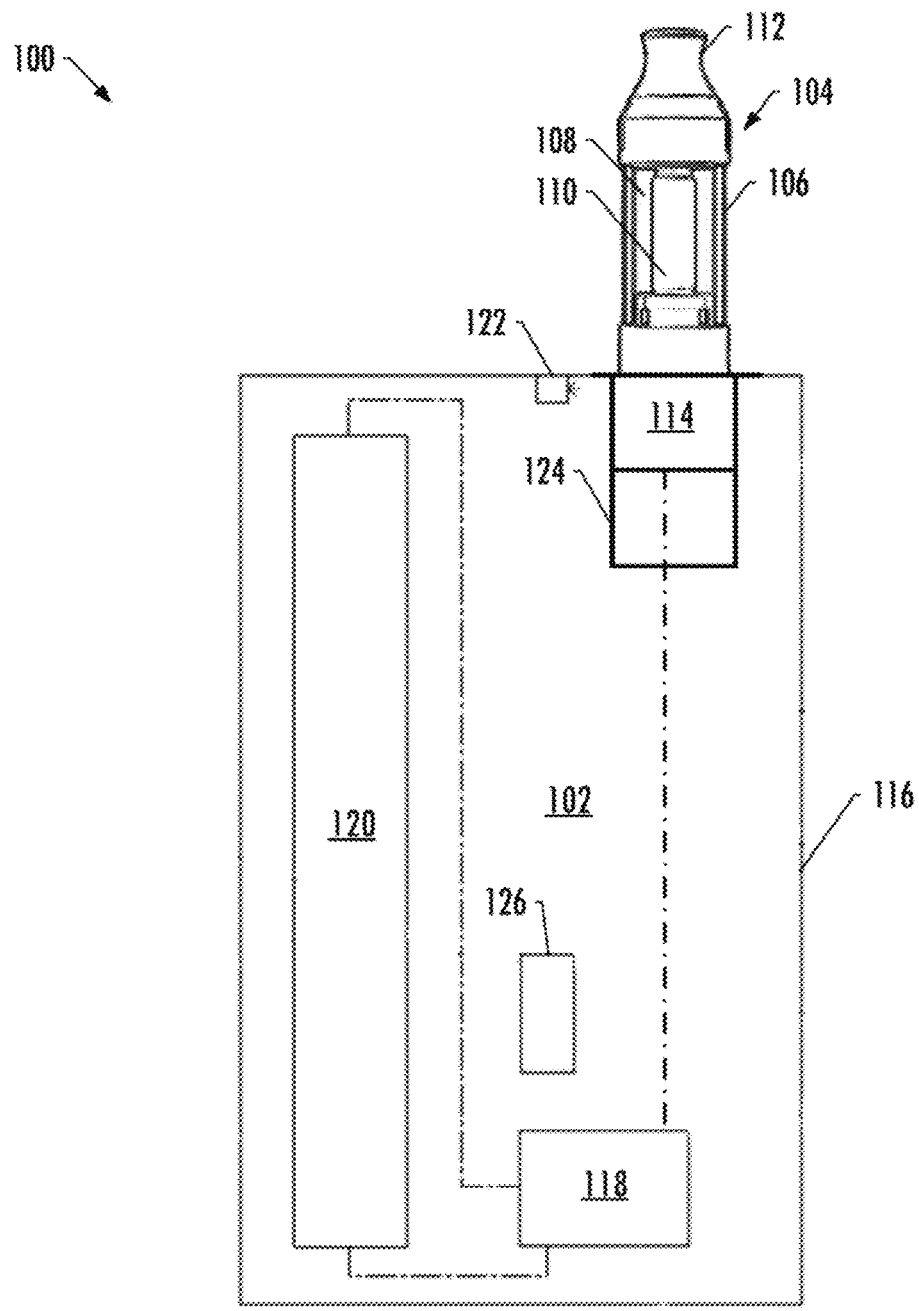

FIG. 1A illustrates a front view of an aerosol delivery device 100, and FIG. 1B illustrates a modified sectional view through the aerosol delivery device (collectively FIG. 1), according to an example implementation of the present disclosure. As illustrated, the aerosol delivery device may include a control body 102 and a tank 104. In particular, FIG. 1 illustrates the control body and the tank coupled to one another. The control body and the tank may be permanently or detachably aligned in a functioning relationship. Various mechanisms may connect the tank to the control body to result in a threaded engagement, a press-fit engagement, an interference fit, a magnetic engagement or the like. In some examples, the aerosol delivery device may be substantially rod-like, substantially tubular shaped, or substantially cylindrically shaped in some example implementations when the tank and the control body are in an assembled configuration. In other examples, further shapes and dimensions are encompassed—e.g., a rectangular or triangular cross-section, multifaceted shapes, or the like. The tank and control body may include a unitary housing or outer body or separate, respective housings or outer bodies, which may be formed of any of a number of different materials. The housing may be formed of any combination of suitable, structurally-sound materials. In some examples, the housing may be formed of at least one of a metal or alloy, such as stainless steel, aluminum or the like. Other suitable materials include various plastics (e.g., polycarbonate or a copolyester), substantially biodegradable plastics (e.g. polyhydroxyalkonates), metal-plating over plastic, glass, and the like.

In some example implementations, one or both of the control body 102 or the tank 104 of the aerosol delivery device 100 may be referred to as being disposable or as being reusable. The aerosol delivery device may include various other components disposed within the control body or tank or otherwise coupled thereto. These components may be distributed between the control body and the tank in any of various manners. For example, the control body may have a replaceable battery or replaceable battery or a rechargeable battery and thus may be combined with any type of recharging technology, including connection to a typical alternating current electrical outlet, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. For example, an adaptor including a USB connector at one end and a control body connector at an opposing end is disclosed in U.S. Pat. Pub. No. 2014/0261495 to Novak et al., which is incorporated herein by reference in its entirety.

In one example implementation, the control body 102 and tank 104 forming the aerosol delivery device 100 may be permanently and/or removably coupled to one another. Examples of aerosol delivery devices that may be configured to be disposable and/or which may include first and second outer bodies that are configured for permanent coupling are disclosed in U.S. Pat. App. No. 2015/0216232 to Bless et al., which is incorporated herein by reference in its entirety. In another example implementation, the tank and control body may be configured in a single-piece, non-detachable form and may incorporate the components, aspects, and features disclosed herein. However, in another example implementation, the control body and tank may be configured to be separable such that, for example, the tank may be refilled or replaced.

FIG. 1B illustrates a more particular example of the aerosol delivery device 100 in which the components are representative of the components that may be present in a suitable control body 102 and a tank 104 and are not intended to limit the scope of control body and tank components that are encompassed by the present disclosure.

The tank 104 can be formed of a tank shell 106 enclosing a reservoir 108 configured to retain the aerosol precursor composition, and including a heater 110 (sometimes referred to as a heating element). In various configurations, this structure may be referred to as a cartridge; and accordingly, the terms "tank," "cartridge" and the like may be used interchangeably to refer to a shell or other housing enclosing a reservoir for aerosol precursor composition, and including a heater.

In some examples, the reservoir 108 of the tank 104 may comprise a refillable reservoir. The reservoir may be configured to retain the aerosol precursor composition. In some example implementations, the reservoir particularly can be formed of a porous material (e.g., a fibrous material) and thus may be referred to as a porous substrate (e.g., a fibrous substrate). A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material, regenerated cellulose, organic cotton, or polyethylene terephthalate can be used. In other example implementations, a carbon material can be used. A reservoir may be substantially in the form of a container and may include a fibrous material included therein. In other implementations, the reservoir may be formed of a glass, plastic, or other materials not explicitly set forth herein.

The reservoir 108 may be in fluid communication with a liquid transport element adapted to wick or otherwise transport an aerosol precursor composition stored in the reservoir housing to the heater 110. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 110. The heater in these examples may be resistive heating element such as a coil. Example materials from which the coil may be formed include Titanium (Ti), Platinum (Pt), Kanthal (FeCrAl), Nichrome, Molybdenum disilicide ($MoSi_2$), molybdenum silicide (MoSi), Molybdenum disilicide doped with Aluminum ($Mo(Si,Al)_2$), Silver Palladium (Ag/Pd) conductive inks, graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices described herein.

A mouthpiece 112 having an opening defined therein may be coupled to the tank shell 106 (e.g., at the mouthend) to allow for egress of formed aerosol from the tank 104.

The tank 104 may also include one or more electronic components, which may include an integrated circuit, a memory component, a sensor, or the like. The electronic components may be adapted to communicate with a control component of the control body and/or with an external device by wired or wireless means. The electronic components may be positioned anywhere within the tank or a base 114 thereof.

As illustrated in FIG. 1B, the control body 102 can be formed of a control body shell 116 that can include a control component 118 (e.g., a printed circuit board (PCB), an integrated circuit, a memory component, a microprocessor, individually or as part of a microcontroller, and the like), a power source 120, and one or more indicators 122 such as light-emitting diodes (LEDs), and such components can be variably aligned. The power source may include, for example, a battery (single-use or rechargeable), supercapacitor or the like. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

The control component 118 may be configured to direct electrical power from the power source 120 to the heater 110 to heat aerosol precursor composition retained in the tank 104 to produce a vapor, which may occur during a user draw on a mouthpiece 112 of the tank. The control component 118 may include a number of electronic components, and in some examples may be formed of an electronic or printed circuit board (PCB) that supports and electrically connects the electronic components. Examples of suitable electronic components include a microprocessor or processor core, an integrated circuit (IC), a memory, and the like.

In some examples, the control component 118 may include a microcontroller with an integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The control body 102 and the tank 104 may include components adapted to facilitate a fluid engagement therebetween. As illustrated in FIG. 1B, the control body can include a connector 124. The base 114 of the tank can be adapted to engage the connector and can include a projection adapted to fit within the connector. Such engagement can facilitate a stable connection between the control body and the tank as well as establish an electrical connection between the battery 120 and control component 118 in the control body, and the heater 110 in the tank. Further, the control body shell 116 can include an air intake, which may be a notch in the shell where it connects to the connector that allows for passage of ambient air around the connector and into the shell where it then passes through the connector and into the tank through the projection.

A connector and a base useful according to the present disclosure are described in U.S. Pat. App. Pub. No. 2014/0261495 to Novak et al., which is incorporated herein by reference in its entirety. However, various other examples of structures, shapes and components may be employed to couple the base to the connector. In some examples the connection between the base of the tank 104 and the connector of the control body 102 may be substantially permanent, whereas in other examples the connection therebetween may be releasable such that, for example, the control body may be reused with one or more additional tanks that may be disposable and/or refillable.

The reservoir 108 illustrated in FIG. 1B can be a container or can be a reservoir, as presently described. For example, the reservoir can be substantially formed into the shape of a tube encircling the interior of the tank shell 106, in this example. An aerosol precursor composition can be retained in the reservoir. Liquid components, for example, can be retained by the reservoir. The reservoir can be in fluid connection with the liquid transport element. The liquid transport element can transport the aerosol precursor composition stored in the reservoir via capillary action to the heater 110 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices as described herein. In particular, specific combinations of heating members and transport elements as further described below may be incorporated into devices.

In use, when a user draws on the aerosol delivery device 100, airflow is detected by a flow sensor, and the heater 110 is activated to vaporize components of the aerosol precursor composition. Drawing upon the mouthpiece 112 of the aerosol delivery device causes ambient air to enter the air intake and pass through the connector 124 and a central opening in a projection of the base 114. In the tank 104, the drawn air combines with the formed vapor to form an aerosol. The aerosol is whisked, aspirated or otherwise drawn away from the heater and out the opening in the mouthpiece of the aerosol delivery device.

An input element 126 may be included with the aerosol delivery device 100. The input element may be included to allow a user to control functions of the device and/or for output of information to a user. For example, a user may utilize the input element to vaporize an aerosol precursor composition and/or activate an on/off function. The input element may comprise a pushbutton or other switch configured to receive an input from a user. When the input element is actuated, the aerosol delivery device may produce an output corresponding to a status of the aerosol delivery device. For example, the aerosol delivery device may output sound, vibration, or light. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some example implementations, a computing device such as a mobile computer (e.g., smartphone, tablet computer) may be used as an input element in addition to or in lieu of an input element 126 on the aerosol delivery device itself. In particular, the aerosol delivery device 100 may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such implementations, application software may be used in connection with the computing device to input control instructions to the aerosol delivery device, such control instructions including, for example, the ability to form an aerosol of specific composition by choosing the nicotine content and/or content of further flavors to be included.

In some examples, the aerosol delivery device 100 may include a number of additional hardware-implemented or software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 118 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 120 may vary over the course of each puff on the device 100 according to a power control mechanism. The device may include a "long puff" safety timer such that in the event that a user or an inadvertent mechanism causes the device to attempt to puff continuously, the control component 118 may control at least one functional element to terminate the puff automatically after some period of time (e.g., four seconds). Further, the time between puffs on the device may be restricted to less than a period of time (e.g., one hundred (100) seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor, such as by permanently disabling the aerosol delivery device in order to prevent inadvertent heating. A puffing limit switch may deactivate the device in the event of a pressure sensor fail causing the device to continuously activate without stopping after the four second maximum puff time.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device 100 most preferably incorporates the control component 118 or another control mechanism for controlling the amount of electric power to the heater 110 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

The aerosol delivery device 100 can also incorporate the flow sensor or another sensor or detector for control of supply of electric power to the heater 110 when aerosol generation is desired (e.g., upon draw during use). As such, for example, there is provided a manner or method of turning off the power supply to the heating element when the aerosol delivery device is not be drawn upon during use, and for turning on the power supply to actuate or trigger the generation of heat by the heating element during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Representative types of aerosol precursor components and formulations also are set forth and characterized in U.S. Pat. No. 7,217,320 to Robinson et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® brand electronic cigarette product by R. J. Reynolds Vapor Company, the BLU™ brand electronic cigarette product by Imperial Tobacco Group PLC, the MISTIC MENTHOL™ brand electronic cigarette product by Mistic Ecigs, and the VYPE™ brand electronic cigarette product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

Figure 2:
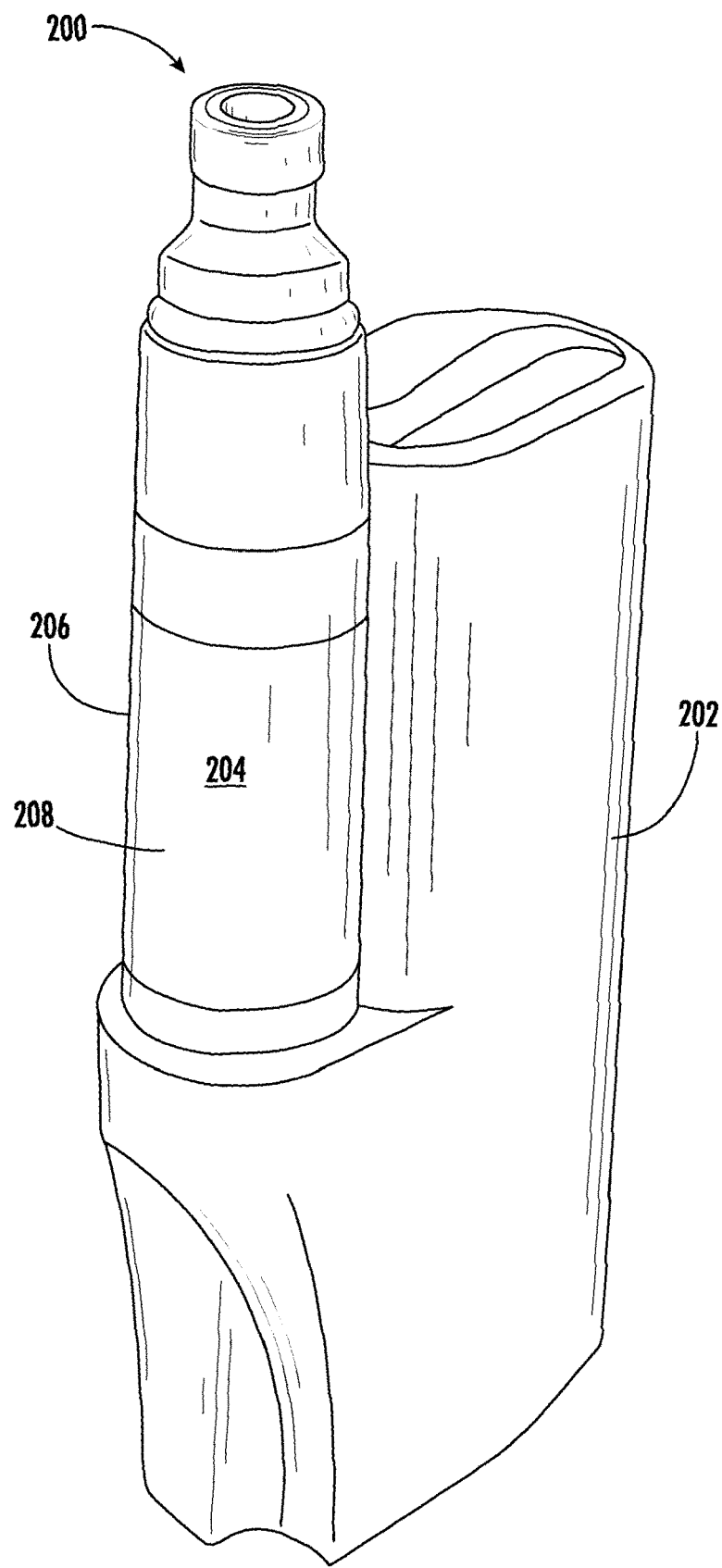

FIG. 2 illustrates a perspective view of a suitable aerosol delivery device 200 that in some examples may correspond to the aerosol delivery device 100 of FIG. 1. As shown, the aerosol delivery device can comprise a control body 202 and a tank 204, which may correspond to respectively the control body 102 and tank 104 of FIG. 1. The control body may define an ergonomic shape configured to comfortably fit within a user's hand. The shape of the housing, however, is not limited and may be any shape that accommodates the various elements as described herein. In some implementations, the housing may be expressly non-cylindrical.

As previously explained, the tank 204 can be formed of a tank shell 206 enclosing a reservoir 208 therein. In some example implementations, the reservoir may be a refillable reservoir, and a container of aerosol precursor composition may be provided for refilling the reservoir. The tank and container may be removably, sealably connectable to one another such that the sealed coupling between the tank and the container may be configured to enable the transfer of aerosol precursor composition between the container and the aerosol delivery device.

Figure 3:
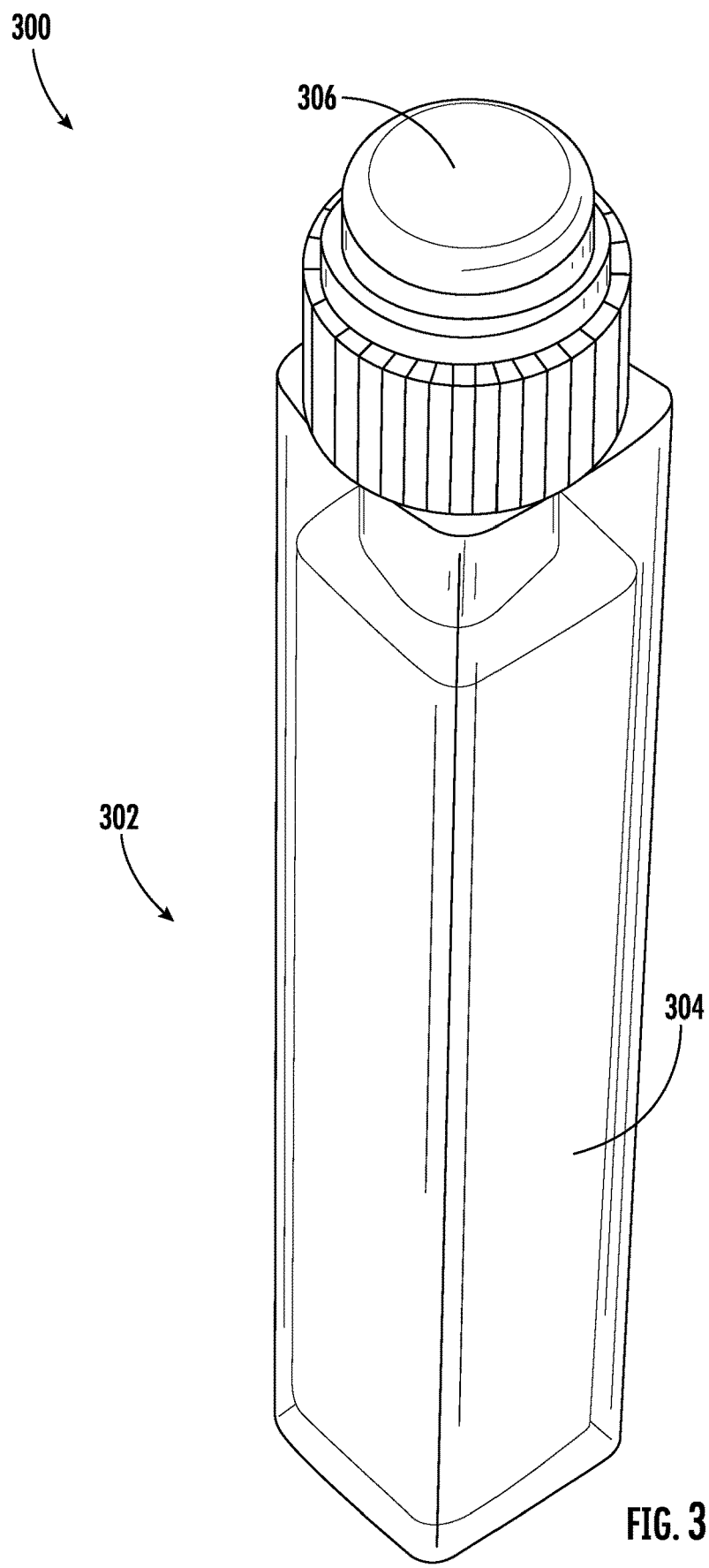

FIG. 3 illustrates a perspective view of a container 300 of aerosol precursor composition, according to various example implementations of the present disclosure. As shown, the container includes a container shell 302 that may comprise a reservoir 304 configured to contain an aerosol precursor composition, and a cap 306 that may be configured to cover a passageway to the reservoir. In particular, FIG. 3 illustrates the container shell and the cap coupled to one another. The container shell and the cap may be removably coupled to one another. Various mechanisms may connect the container shell to the cap to result in a threaded engagement, a press-fit engagement, an interference fit, a magnetic engagement or the like. In some examples, the container may be substantially rod-like, substantially tubular shaped, or substantially cylindrically shaped. In other examples, further shapes and dimensions are encompassed—e.g., a rectangular or triangular cross-section, multifaceted shapes, or the like.

The container 300 may be formed of any of a number of different materials. The container shell 302 and cap 306 may be formed of any combination of suitable, structurally-sound materials, and may be formed of the same or different materials. In some examples, the container shell and cap may be formed of at least one of a metal or alloy, such as stainless steel, aluminum or the like. Other suitable materials include various plastics (e.g., polycarbonate), metal-plating over plastic, glass, and the like.

Figure 4:
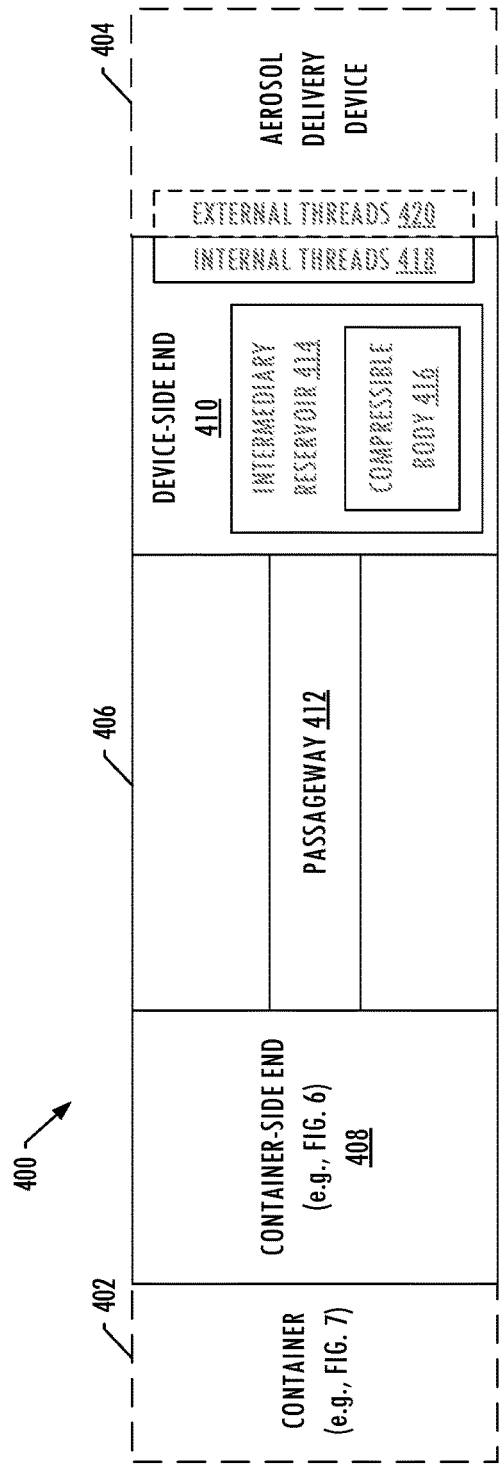

In various contained liquid systems for refilling aerosol delivery devices, a container for refilling an aerosol delivery device may be configured to mate with only a corresponding tank of a compatible aerosol delivery device, and vice versa. FIG. 4 illustrates an adapter to allow a user to mate their container with an otherwise incompatible aerosol delivery device. And FIG. 5 conversely illustrates an adapter to allow a user to mate their aerosol delivery device with an otherwise incompatible container.

In particular, FIG. 4 illustrates an adapter 400 for mating a container 402 of aerosol precursor composition with an aerosol delivery device 404 having a refillable reservoir. More particularly, the adapter may be for mating the container with an otherwise incompatible aerosol delivery device. In some examples, the container and aerosol delivery device may correspond to respectively the container 300 of FIG. 3 and aerosol delivery device 100 of FIG. 1 (one example of which may be aerosol delivery device 200 of FIG. 2). An example of a suitable container 402 to which the otherwise incompatible aerosol delivery device 404 may be mated is disclosed in U.S. patent application Ser. No. 14/802,667, filed Jul. 7, 2015, to O'Brien et al., which is incorporated herein by reference in its entirety.

The adapter 400 may comprise a body 406 having a container-side end 408 and an opposing, device-side end 410 that are sealably connectable with respectively the container 402 and the aerosol delivery device 404. The body may define a passageway 412 between the container-side and device-side ends for transfer of aerosol precursor composition from the container into the refillable reservoir of the aerosol delivery device.

As described above, the device-side end 410 of the adapter 400 may be sealably connectable with the aerosol delivery device 404. In some example implementations, the device-side end defines an intermediary reservoir 414 between the passageway 412 and the aerosol delivery device upon engaging the aerosol delivery device. The intermediary reservoir may define a compressible body 416 configured to receive aerosol precursor composition from the container via the passageway. In response to being compressed, the intermediary reservoir may force at least some of the aerosol precursor composition from the intermediary reservoir into the refillable reservoir of the aerosol delivery device.

The device-side end 410 may be configured to sealably connect with the aerosol delivery device 404 in any of a number of different manners. In some implementations, for example, the device-side end is internally threaded 418, and thereby threadable onto an externally threaded portion 420 of the aerosol delivery device. The externally threaded portion of the aerosol delivery device may define an opening to the refillable reservoir of the aerosol delivery device. In another example implementation, at least an inner cavity of the device-side end defines a sheath sized to receive at least a portion of the aerosol delivery device therein for connection therewith.

The device-side end 410 may be configured to sealably connect with the aerosol delivery device 404 in any of a number of different manners. In some implementations, for example, the device-side end is internally threaded, and thereby threadable onto an externally threaded portion of the aerosol delivery device. The externally threaded portion of the aerosol delivery device may define an opening to the refillable reservoir of the aerosol delivery device. In another example implementation, at least an inner cavity of the device-side end defines a sheath sized to receive at least a portion of the aerosol delivery device therein for connection therewith.

Figure 5:
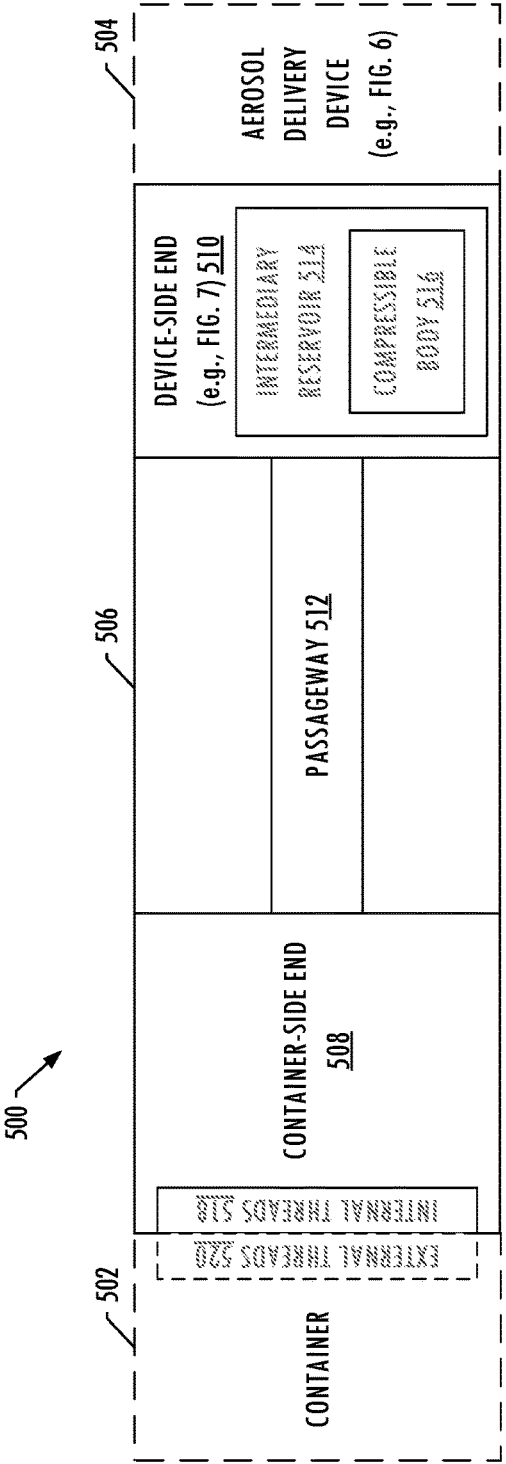

As indicated above, FIG. 5 illustrates an adapter 500 for mating a container 502 of aerosol precursor composition with an aerosol delivery device 504 having a refillable reservoir. More particularly, the adapter may be for mating the aerosol delivery device with an otherwise incompatible container. In some examples, the container and aerosol delivery device may correspond to respectively the container 300 of FIG. 3 and aerosol delivery device 100 of FIG. 1 (one example of which may be aerosol delivery device 200 of FIG. 2). An example of a suitable aerosol delivery device 504 to which the otherwise incompatible container 502 may be mated is disclosed in U.S. patent application Ser. No. 14/802,667, filed Jul. 7, 2015, to O'Brien et al., which is incorporated herein by reference in its entirety.

The adapter 500 may comprise a body 506 having a container-side end 508 and an opposing device-side end 510 that are sealably connectable with respectively the container and the aerosol delivery device. The body may define a passageway 512 between the container-side end and device-side end for transfer of aerosol precursor composition from the container into the refillable reservoir. The adapter 500 may be coupled to an opening in a shell of the container. As such, the adapter may be shaped and sized to match the opening of the container shell.

As described above, the container-side end 508 of the adapter 500 may be sealably connectable with the container 502 of aerosol precursor composition. In some example implementations, the container-side end defines an intermediary reservoir 514 between the passageway 512 and the container upon connection with the container. The intermediary reservoir may define a compressible body 516 configured to receive aerosol precursor composition from the container. In response to being compressed, the intermediary reservoir may force at least some of the aerosol precursor composition from the intermediary reservoir into the device-side end via the passageway.

The container-side end 508 may be configured to sealably connect with the container 502 in any of a number of different manners. In some implementations, for example, the container-side end is internally threaded 518, and thereby threadable onto an externally threaded portion 520 of the container. The externally threaded portion of the container may define an opening to a reservoir of aerosol precursor composition of the container. In another example implementation, at least an inner cavity of the container-side end defines a sheath sized to receive at least a portion of the container therein for connection therewith.

Figure 6:
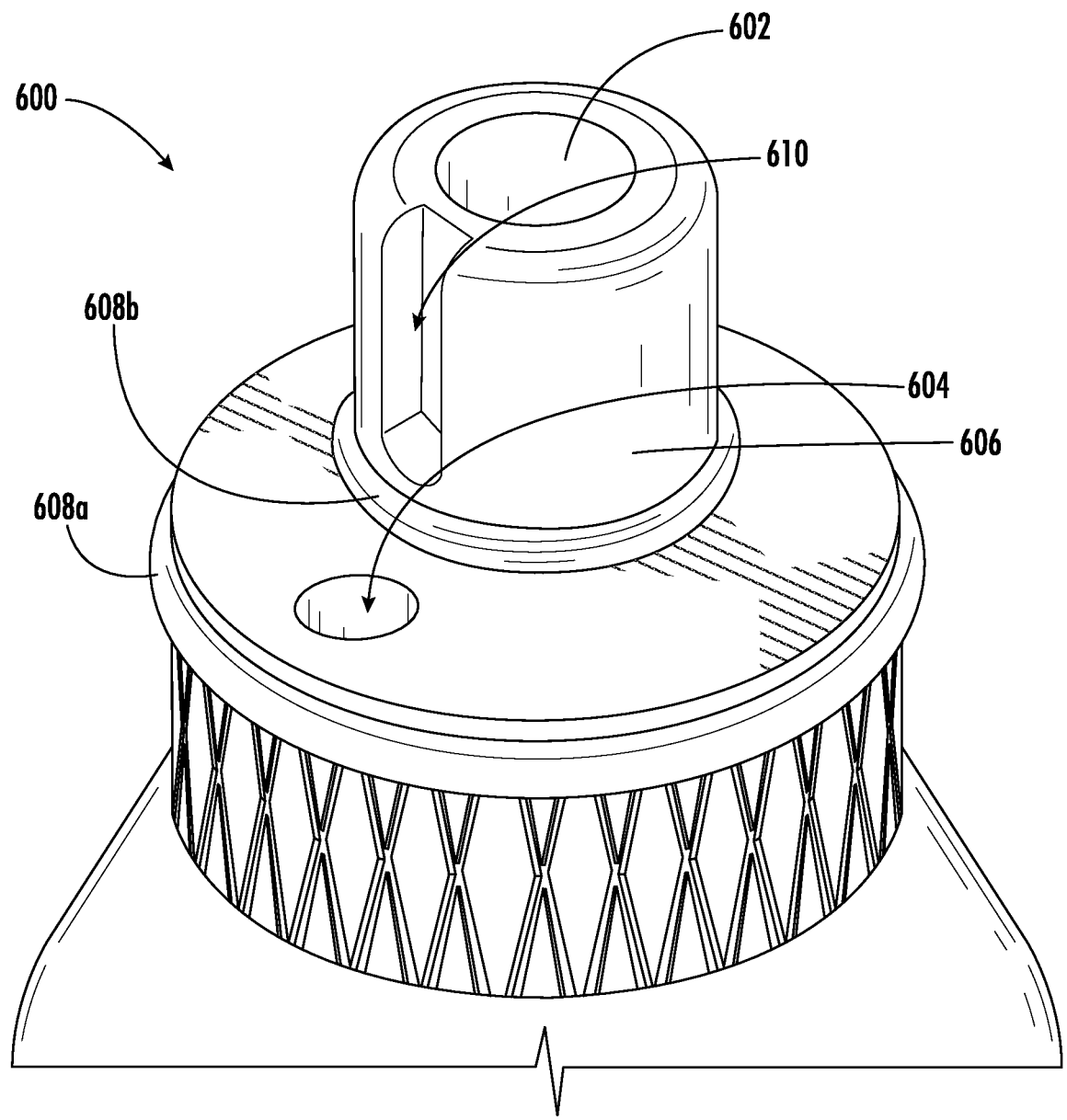
Figure 7A:
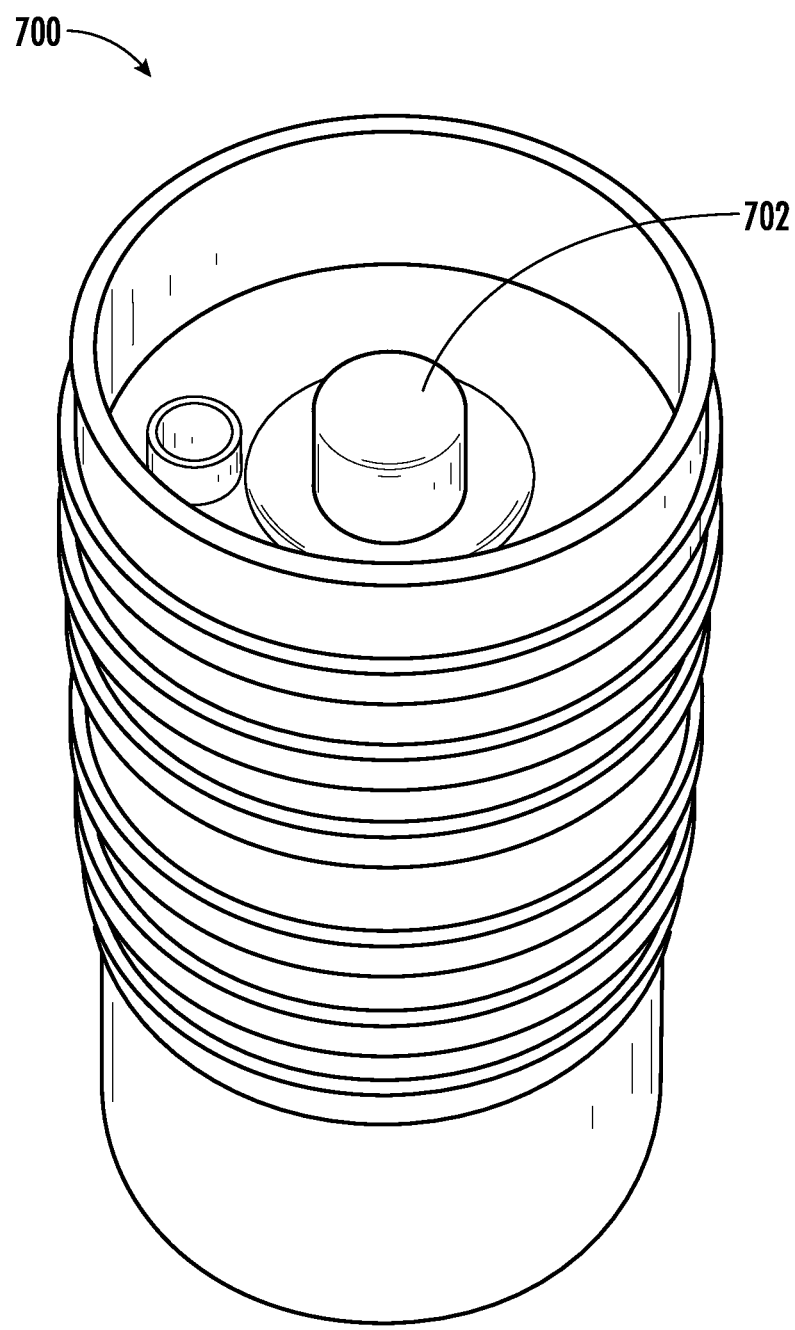
Figure 7C:
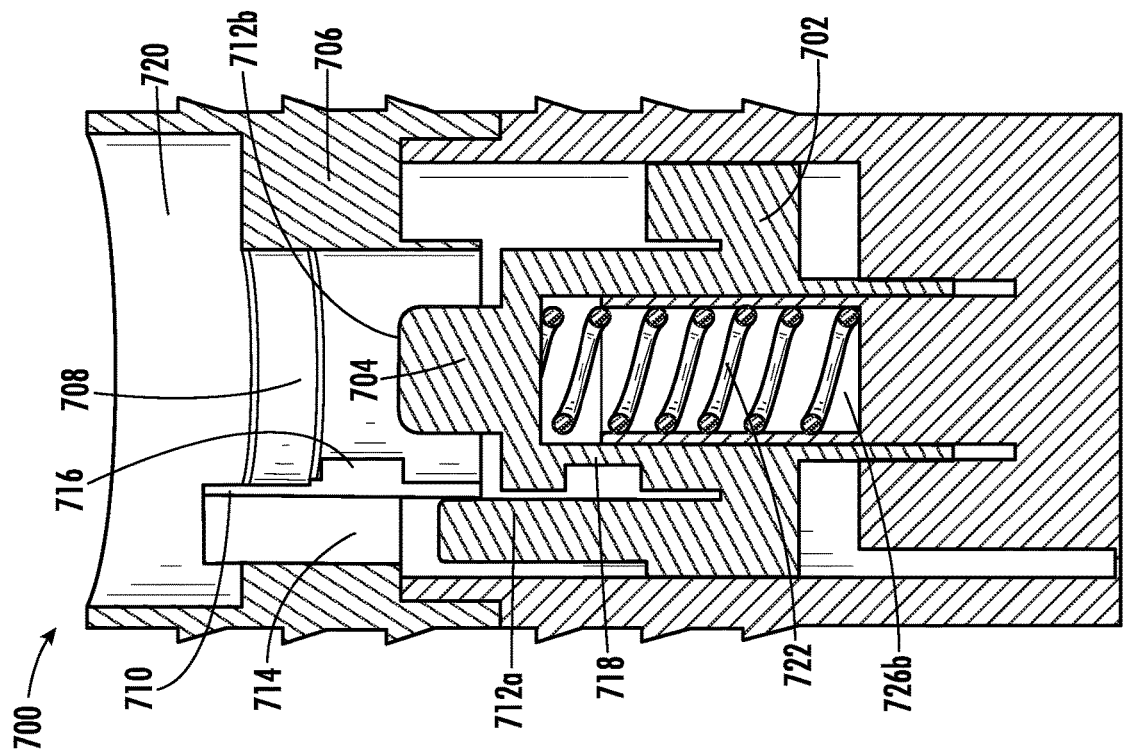
Figure 7B:
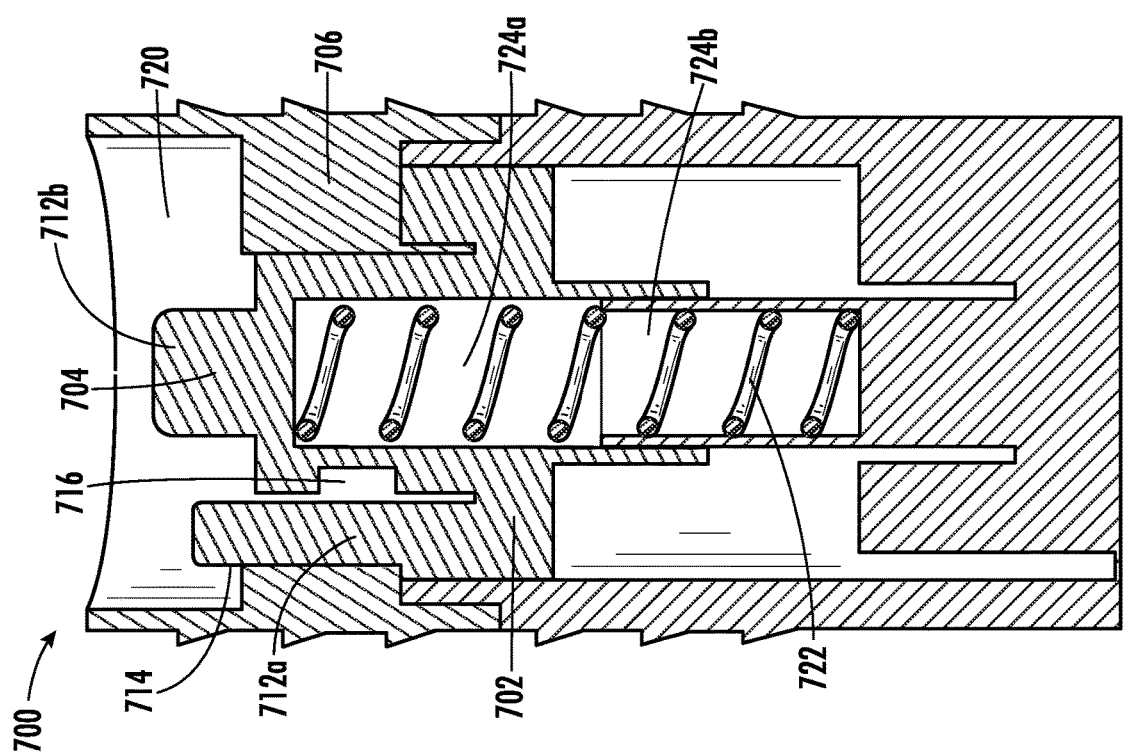
Figure 7D:
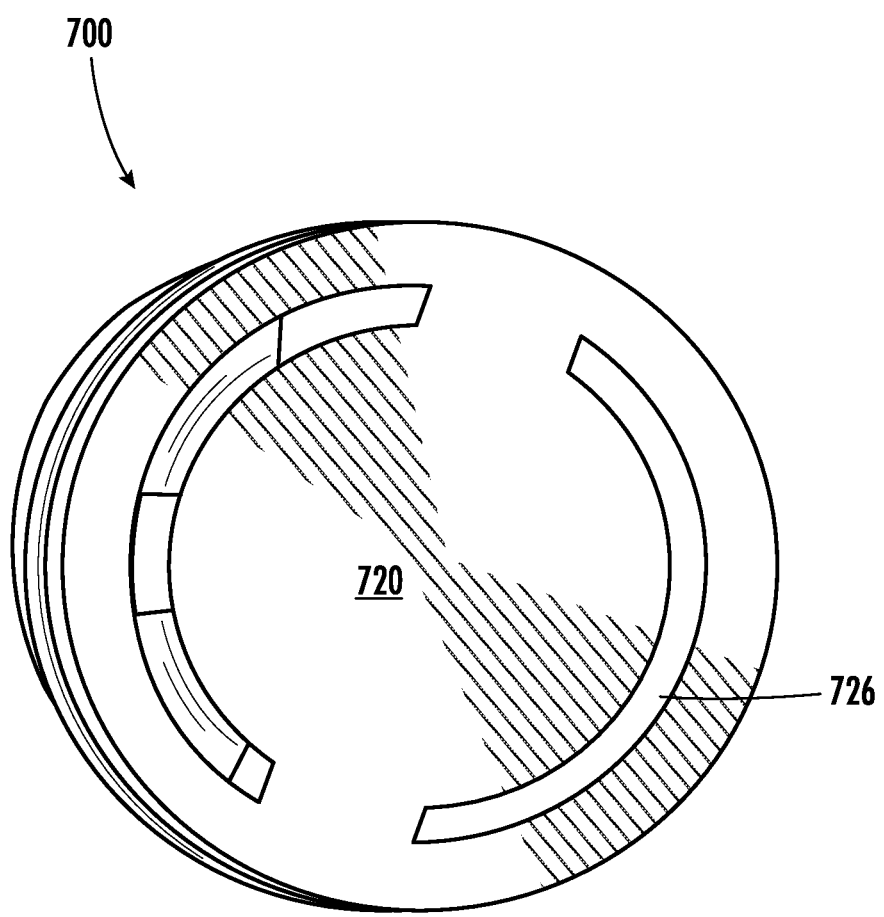

FIGS. 6 and 7 (including FIGS. 7A-7D) illustrate respective apparatuses 600, 700 that may be configured to mate with one another, and function as various elements of the adapters 400, 500, containers 402, 502 and aerosol delivery devices 404, 504 of FIGS. 4 and 5, according to some example implementations. For example, the apparatus 600 of FIG. 6 may function as the container-side end 408 of the adapter 400 of FIG. 4, and the apparatus 700 of FIG. 7 may form a portion of the container 402 configured to mate with the apparatus 600 (container-side end 408). Likewise, for example, the apparatus 700 of FIG. 7 may function as the device-side end 510 of the adapter 500 of FIG. 5, and the apparatus 600 of FIG. 6 may form a portion of the aerosol delivery device 504 configured to mate with the apparatus 700 (device-side end 510).

In some example implementations, the apparatus 600 (e.g., container-side end 408 or aerosol delivery device 504) may be configured to engage a valve 702 of the corresponding apparatus 700 (e.g., container 402 or device-side end 510) during refilling of the reservoir. The apparatus may define a separate and distinct first 602 and second port 604. In some example implementations, in which the apparatus functions as the container-side end, the first and second port may respectively correspond to a mating port and filling port. In other example implementations, in which the apparatus functions as a portion of the aerosol delivery device, the first and second ports may respectively correspond to an airflow port and filling port. In these example implementations, the airflow port may be for the flow of air through a portion of the aerosol delivery device when the valve and the aerosol delivery device are disengaged, such as during use of the aerosol delivery device.

As used herein, a port may refer to a narrow and elongated passageway through which liquid, air, and the like may be transported. As illustrated in FIG. 6, in one example implementation, the ports may be substantially cylindrically shaped so as to allow for the smooth transfer of liquid and/or air. In other example implementations, further shapes and dimensions may be encompassed—e.g., a rectangular or triangular cross-section, multifaceted shapes, or the like. In further examples, the internal walls of the port may contain a micropatterned surface as to promote wettability and fluid flow through the port.

The first port 602 of the apparatus 600 may define an inner cavity sized to receive therein a matching portion 704 of the valve 702 of the corresponding apparatus 700 for connection therewith. The first port may be closed by the valve during engagement between the valve and the apparatus to prevent the aerosol precursor composition from passing through the first port.

In some example implementations, the apparatus 600 may include an adapter protrusion 606 in which the first port 602 may be defined. Upon sealably connecting the apparatus and the corresponding apparatus 700, the adapter protrusion may be brought into direct engagement with at least a portion of the corresponding apparatus such that the two mate with one another. In some examples, the corresponding apparatus includes a nozzle 706 within which the valve 702 is movably positioned. The nozzle may include a cavity 708 sized to receive therein at least a portion of the valve when the apparatus and valve are disengaged, and the adapter protrusion when the apparatus and valve are engaged.

In some example implementations, in which the apparatus 600 functions as a portion of the aerosol delivery device 504, the adapter protrusion may be positioned beneath a removably coupleable mouthpiece of the aerosol delivery device when the mouthpiece is coupled to the aerosol delivery device.

The second port 604 of the apparatus 600 may be for transfer of aerosol precursor composition from the container into a refillable reservoir of the aerosol delivery device during engagement of the apparatus and a valve 702 of the corresponding apparatus 700. In some examples, the nozzle 706 of the corresponding apparatus may also include a spout 710 therein for transfer of aerosol precursor composition from the container into the reservoir, in which the second port may be sized to receive the spout when the apparatus and valve are engaged. In some example implementations, the spout contains a micro-patterned internal surface.

The apparatus 600 may further include one or more seals to secure the connection with and between the corresponding apparatus 700. In particular, a first seal 608a may be positioned around the perimeter of the apparatus such that it provides a seal between the nozzle 706 and the apparatus during engagement with the corresponding apparatus. Similarly, a second seal 608b may be positioned around the perimeter of the apparatus (beneath a slot 610 of the apparatus) such that it provides a seal between the valve 702 and the apparatus during engagement with the corresponding apparatus. The seal may be formed of any combination of suitable, structurally-sound materials. In some examples, the seal may be formed of at least one of a gasket material, elastomeric material, or the like.

The valve 702 of the corresponding apparatus 700 may include a depressible valve body including a first valve member 712a and a second valve member 712b. The first valve member may open or close a passageway 714 to aerosol precursor composition stored within the container. In particular, the first valve member may include a projection that is sized to fit and/or sealably engage the passageway thereby further restricting the release of aerosol precursor composition from a reservoir of the container when the valve is not depressed during engagement with the aerosol delivery device.

The second valve member 712b may close the first port 602 of the apparatus 600 when the valve body is depressed during engagement with the apparatus. As previously indicated, the first port may define an inner cavity, and the second valve member may include the matching portion 704 in which the inner cavity of the first port may be sized to receive therein the matching portion of the second valve member.

In some example implementations, the apparatus 600 and corresponding apparatus 700 may include one or more interface features. For example, the apparatus may include a slot 610 mateable with a matching tab 716 of the corresponding apparatus to align the apparatus for connection therewith. In particular, the slot may align the second port 604 of the apparatus and the spout 710 of the corresponding apparatus to ensure proper engagement between the two. Similarly, the second valve member 712b of the valve 702 may also comprise a slot 718 mateable with the tab such that the valve may be movably positioned within the valve cavity 708 around the tab.

In particular, a housing 720 of the nozzle 706 may be coupled with the valve 702 via a spring 722 in which the spring may be configured to compress when the valve is depressed and extend when the valve is not depressed. The spring may be positioned within a spring cavity 724a of the second valve member 706b and a spring cavity 724b of the nozzle housing such that the valve may be movably positioned within the valve cavity around the tab 714. The nozzle may be positioned over the valve within at least a portion of the nozzle housing such that a sealed connection is provided between the nozzle and the nozzle housing.

The housing 720 of the nozzle 706 may define one or more liquid ports 726 configured to allow the transfer of aerosol precursor composition from a passageway (e.g., passageway 512) into the corresponding apparatus 700. The base of the valve may be shaped such that it allows for fluid engagement between the passageway of the adapter and the interior of the nozzle to allow the aerosol precursor composition to pass from the container (e.g., container 502) reservoir through the bottom of the nozzle via the passageway. In some example implementations, the base of the valve may be cross-shaped so as to allow the passage of aerosol precursor composition throughout the valve cavity of the nozzle.

FIG. 8 illustrates various operations in a method 800 of mating a container of aerosol precursor composition with an aerosol delivery device having a refillable reservoir for refilling the aerosol delivery device according to an example implementation of the present disclosure. As shown in block 802, the method may include sealably connecting an adapter with the container and aerosol delivery device. The adapter may comprise a body having a container-side end and an opposing device-side end that are sealably connectable with respectively the container and aerosol delivery device. The body may define a passageway therebetween for transfer of aerosol precursor composition from the container into the refillable reservoir. As shown at block 804, the method may also include transferring aerosol precursor composition from the container through the passageway and into the reservoir to thereby refill the reservoir.

In one example implementation of the method 800, the container-side end may be configured to engage a valve of the container during refilling of the reservoir. The container-side end may define separate and distinct filling and mating ports. The mating port may define an inner cavity sized to receive therein a matching portion of the valve for connection therewith. The filling port may be for transfer of aerosol precursor composition from the container into the refillable reservoir during engagement of the container-side end and valve.

In another example implementation of the method 800, the device-side end may include a valve configured to engage the aerosol delivery device during refilling of the reservoir. The aerosol delivery device may define separate and distinct filling and airflow ports. The airflow port may be for a flow of air through a portion of the aerosol delivery device when the valve and aerosol delivery device are disengaged. The filling port may be for transfer of aerosol precursor composition from the container into the refillable reservoir during engagement of the valve and the aerosol delivery device in which the airflow port is closed by the valve to prevent the aerosol precursor composition from passing through the airflow port.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1A-7 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An adapter for mating a container of aerosol precursor composition with an aerosol delivery device having a reservoir that is refillable, the aerosol delivery device defining separate and distinct filling and airflow ports that are elongated passageways through which liquid or air is transportable, the adapter separate and distinct from the container and the aerosol delivery device, the adapter comprising:
    a body having a container-side end and an opposing, device-side end, the container-side end configured to connect with the container, and the device-side end configured to engage the aerosol delivery device, the device-side end defining a first passageway portion extending into the body, and the body defining a second passageway portion in fluid communication with the first passageway portion and extending from within the body to the container-side end; and
    a valve located at the device-side end and configured to regulate the transfer of aerosol precursor composition from the container into the reservoir via the second passageway portion, the first passageway portion and the filling port, the valve including:
    a valve body that is depressible, monolithic and defines a first valve member and a second valve member, the valve body and thereby the first valve member and the second valve member configured to depress when the device-side end is engaged with the aerosol delivery device, the first valve member configured to open the first passageway portion to enable the transfer of the aerosol precursor composition, and the second valve member configured to close the airflow port of the aerosol delivery device to prevent passage of the aerosol precursor composition through the airflow port.

2. The adapter of claim 1, wherein a portion of the second valve member matches an inner cavity of the airflow port, the portion of the second valve member sized to be received within the inner cavity of the airflow port when the device-side end is engaged with the aerosol delivery device and the valve body is depressed.

3. The adapter of claim 1, wherein the valve body is depressed by a protrusion of the aerosol delivery device within which the airflow port is defined, when the device-side end is engaged with the aerosol delivery device, and
    wherein the device-side end includes a nozzle within which the valve is movably positioned, the nozzle defining a cavity sized to receive the second valve member when the device-side end is disengaged with the aerosol delivery device, and receive the protrusion of the aerosol delivery device when the device-side end is engaged with the aerosol delivery device and the valve body is depressed.

4. The adapter of claim 3, wherein the nozzle includes a spout that is aligned with the first passageway portion and projects from a surface of the nozzle, and that is sized to be received within the filling port when the device-side end is engaged with the aerosol delivery device and the valve body is depressed.

5. The adapter of claim 4, wherein the spout has a micro-patterned internal surface to promote the transfer of the aerosol precursor composition.

6. The adapter of claim 3, wherein the nozzle further defines a tab within the cavity that is configured to mate with a matching slot defined on an outer surface of the protrusion of the aerosol delivery device, to align the device-side end with the aerosol delivery device when the device-side end is engaged with the aerosol delivery device.

7. The adapter of claim 1, wherein the device-side end further defines an intermediary reservoir with a compressible body between the first passageway portion and the second passageway portion, the compressible body configured to receive aerosol precursor composition from the container via the second passageway portion, and force at least some of the aerosol precursor composition through the first passageway portion when compressed.

8. The adapter of claim 1, wherein the container-side end is threaded and thereby threadable onto the container to connect the container-side end with the container.

9. The adapter of claim 1, wherein the container-side end defines a sheath sized to receive at least a portion of the container inside the sheath to connect the container-side end with the container.

10. A method of mating a container of aerosol precursor composition with an aerosol delivery device having a reservoir that is refillable, the aerosol delivery device defining separate and distinct filling and airflow ports that are elongated passageways through which liquid or air is transportable, the method comprising:
    connecting an adapter with the container, the adapter separate and distinct from the container and the aerosol delivery device, the adapter having a body having a container-side end and an opposing, device-side end, connecting the adapter with the container including connecting the container-side end with the container;
    engaging the adapter with the aerosol delivery device, including engaging the device-side end with the aerosol delivery device, the device-side end defining a first passageway portion extending into the body and a second passageway portion in fluid communication with the first passageway portion and extending from within the body to the container-side end; and
    transferring aerosol precursor composition from the container into the reservoir via the second passageway portion, the first passageway portion and the filling port, the adapter further including a valve located at the device-side end that regulates the transfer of aerosol precursor composition, the valve including a valve body that is depressible, monolithic and defines a first valve member and a second valve member, wherein engaging the device-side end with the aerosol delivery device includes depressing the valve body and thereby the first valve member and the second valve member depressed, the first valve member opening the first passageway portion to enable the transfer of the aerosol precursor composition, and the second valve member closing the airflow port of the aerosol delivery device to prevent passage of the aerosol precursor composition through the airflow port.

11. The method of claim 10, wherein a portion of the second valve member matches an inner cavity of the airflow port, and engaging the device-side end with the aerosol delivery device includes receiving the portion of the second valve member within the inner cavity of the airflow port when the valve body is depressed.

12. The method of claim 10, wherein engaging the device-side end with the aerosol delivery device includes depressing the valve body by a protrusion of the aerosol delivery device within which the airflow port is defined, and wherein the device-side end includes a nozzle within which the valve is movably positioned, the nozzle defining a cavity sized to receive the second valve member when the device-side end is disengaged with the aerosol delivery device, and engaging the device-side end with the aerosol delivery device also includes receiving the protrusion of the aerosol delivery device within the cavity when the valve body is depressed.

13. The method of claim 12, wherein the nozzle includes a spout that is aligned with the first passageway and projects from a surface of the nozzle, and engaging the device-side end with the aerosol delivery device includes receiving the spout within the filling port when the valve body is depressed.

14. The method of claim 13, wherein the spout has a micro-patterned internal surface to promote the transfer of the aerosol precursor composition.

15. The method of claim 12, wherein the nozzle further defines a tab within the cavity, and engaging the device-side end with the aerosol delivery device includes mating the tab with a matching slot defined on an outer surface of the protrusion of the aerosol delivery device, to align the device-side end with the aerosol delivery device.

16. The method of claim 10, wherein the device-side end further defines an intermediary reservoir with a compressible body between the first passageway portion and the second passageway portion, and transferring the aerosol precursor composition includes the compressible body receiving the aerosol precursor composition from the container via the second passageway portion, and compressing the compressible body to force at least some of the aerosol precursor composition through the first passageway portion.

17. The method of claim 10, wherein the container-side end is threaded, and connecting the container-side end with the container includes threading the container-side end onto the container.

18. The method of claim 10, wherein the container-side end defines a sheath, and connecting the container-side end with the container includes receiving at least a portion of the container inside the sheath.

* * * * *